United States Patent [19]
Grant

[11] Patent Number: 5,105,828
[45] Date of Patent: Apr. 21, 1992

[54] BACK, ABDOMEN AND POSTURE SUPPORTING AND RETAINING JOHNSON BELT

[76] Inventor: Richard O. Grant, 121 Jackson St., Roanoke Rapids, N.C. 27870

[21] Appl. No.: 645,646

[22] Filed: Jan. 25, 1991

[51] Int. Cl.⁵ .......................... A61F 5/37; A61F 5/02
[52] U.S. Cl. ...................... 128/876; 602/19
[58] Field of Search .................. 128/78, 85, 86, 87 R, 128/870, 875, 876, 877, 100.1, 102.1, 104.1, 107.1, 116.1

[56] References Cited

U.S. PATENT DOCUMENTS

| | | | |
|---|---|---|---|
| 2,726,714 | 12/1955 | McAndrews | 128/876 |
| 2,828,737 | 4/1958 | Hale | 128/78 |
| 2,917,044 | 12/1959 | Bassin | 128/876 |
| 3,467,085 | 9/1969 | Cormier | 128/876 |
| 3,817,245 | 6/1974 | Kroeger | 128/876 |
| 4,132,229 | 1/1979 | Morrison | 128/876 |
| 4,173,973 | 11/1979 | Hendricks | 128/78 |
| 4,175,548 | 11/1979 | Henry | 128/78 |
| 4,691,696 | 9/1987 | Farfan de los Godos | 128/78 |
| 4,976,257 | 12/1990 | Akin | 128/78 |

Primary Examiner—Robert A. Hafer
Assistant Examiner—Michael Brown
Attorney, Agent, or Firm—Joseph J. Zito

[57] ABSTRACT

A posture support and patient retainer device for a seated individual, having an essentially rigid plate secured against the lower front abdomen of the wearer by a strap system including either a single or double strap extending around the wearer and the seat. The device is utilized to provide posture support for relief of pain and strain associated with prolonged seating and to retain or assist infirm individuals in remaining seated.

15 Claims, 4 Drawing Sheets

BACK, ABDOMEN AND POSTURE SUPPORTING AND RETAINING JOHNSON BELT

BACKGROUND OF THE INVENTION

The present invention relates to devices for supporting and/or retaining an individual in a seated, reclining or prone position. More specifically, the present invention relates to a posture support device which wraps around an individual and their standard chair, wheelchair or bed, to assist in retaining the wearer while preventing them from falling out of the bed or chair or from sliding out of position while maintaining a comfortable and proper seated or reclined position.

Individuals who must remain seated for extended periods of time often develop back strain or pain. Proper posture support for these individuals can aid in relief of this strain. Infirm individuals, such as hospital patients or individuals confined to wheelchairs often find it difficult to assume or maintain a proper seated position, which can result in extreme discomfort or risk of serious injury. A device which provides proper support can relieve pain and discomfort associated with prolonged sitting. A device which can offer appropriate support can aid in comfortable and safe use of wheelchairs and can allow infirm individuals to maintain a seated position without constant attendance.

Prior to the advent of the present invention, there existed a need for a device which could provide appropriate support for these individuals without being overly restrictive. Two factors, slumping and slippage of the wearer, must be considered in the design of an effective supporting/retaining device. Slippage occurs when the wearer slides downwardly out of the retainer device. This can occur when the wearer is inadequately retained thereby allowing enough slack between the wearer and the device to permit movement. If the device allows for forward movement of lower body, the wearer can slip. Slumping occurs when the wearer is able to bend forward or double-over while wearing the device. This can occur if the device affords insufficient support to maintain an appropriate wearer posture.

A number of patient retaining devices are taught in the art, including the retraining belts of Berl and Murcott taught in U.S. Pat. Nos. 3,100,484 and 3,536,457, respectively. The straps taught therein are narrow and soft and do not adequately protect against slumping or slippage of the patient. Further, the Murcott device is cumbersome to apply and requires access behind the patient necessitating movement of the patient.

U.S. Pat. No. 4,170,991 to Kella and U.S. Pat. No. 3,612,605 to Posey teach retainer devices which secure both the abdomen and chest of the patient utilizing a second set of straps which are placed just beneath the arm or over the shoulders, respectively. Kella teaches the use of a seat bib which requires the patient to be removed from the chair to install the bib. The Posey device commonly known as a "Posey Vest" is currently in wide spread use in hospitals for support of patients. The vest requires cumbersome securing of both waist and shoulder straps. Although the vest prevents slumping, or a direct lean forward of the patient, the device is insufficient to retain the patient from slipping down in the vest. The shoulder straps then present a danger of strangulation for patients who are unable to extricate themselves after slippage.

The strap taught in Spann, U.S. Pat. No. 4,108,170, is also too soft and deformable to adequately prevent slumping. While this strap is easy to apply, the high location necessitated by its configuration prevents the strap from implementing posture support and renders the strap ineffective at deterring downward slippage of the patient.

A number of retaining devices are also taught in the art for support of infants or children. These devices, illustrated for example in the U.S. Pat. Nos. 579,818; 2,739,642; 4,861,109; 4,867,464; and 4,781,210, while teaching devices which provide support, do not provide the support capabilities of the present invention and are cumbersome and restrictive.

Also known in the art are seat belt protectors such as illustrated in U.S. Pat. Nos. 3,241,881 and 3,300,247. U.S. Pat. No. 4,487,201 teaches a flexible suspension band which acts to support a portion of the weight of the individual while in a seated position.

SUMMARY OF THE INVENTION

It is an object of the present invention to provide support in a single easily implemented device which provides essential but minimal restrictions on the wearers movements.

It is another object of the invention to provide a device which aids in the safe use of wheelchairs and/or standard chairs.

It is a further object of the present invention to provide a device which is easily sterilized and allows for inexpensive replacement of components.

It is an object of the present invention to provide maximal support with minimal weight and minimal complexity.

It is another object of the present invention to provide sufficient posture support through a rigid supportive structure while maintaining comfort and minimal restriction of the wearer.

The Johnson Belt taught through the exemplary embodiment described herein satisfies these and other objects. The present invention, in either the one piece strap or two piece double strap design, allows for ease of application about both patient and his chair or bed. The use of the removable single or dual strap system allows for easy replacement of the entire strap system in the event of wear or damage.

The design of the present invention teaches a one-size-fits-all devices which allows for universal application.

The broad, stiff abdominal plate taught in the present invention distributes support force to securely hold the upper and lower body, reducing both slumping and slipping.

The removable cushion provides patient comfort and allows for sterility by replacement or cleaning of cushion.

BRIEF DESCRIPTION OF THE DRAWINGS

For a better understanding of the nature of the present invention, reference is had to the following figures and detailed description, wherein like elements are accorded like reference numerals, and wherein.

DETAILED DESCRIPTION OF PREFERRED EXEMPLARY EMBODIMENTS

Figure 3:
FIG. 3 is a side perspective view illustrating the device utilized as a posture support for a seated wearer such as a driver.
Figure 1:
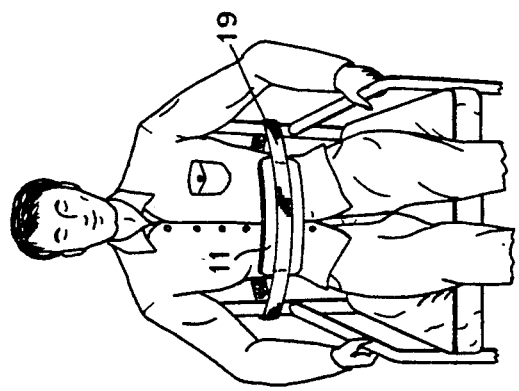
FIG. 1 is a front perspective view of the present invention applied to retain a patient in a wheel chair.
Figure 2A:
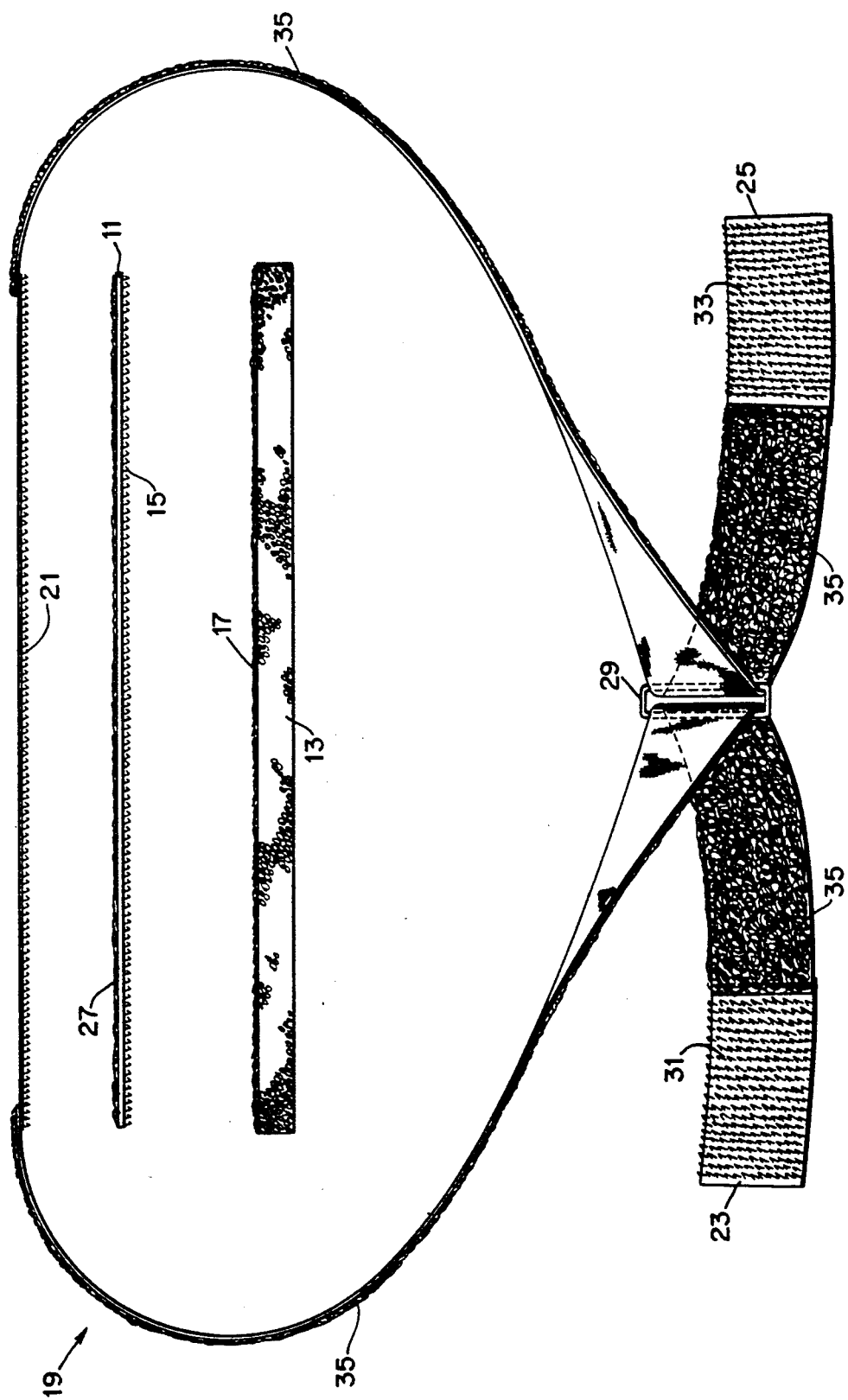
FIG. 2A is a top assembly view of a single strap embodiment of the present invention, illustrating the separate components.
Figure 2B:
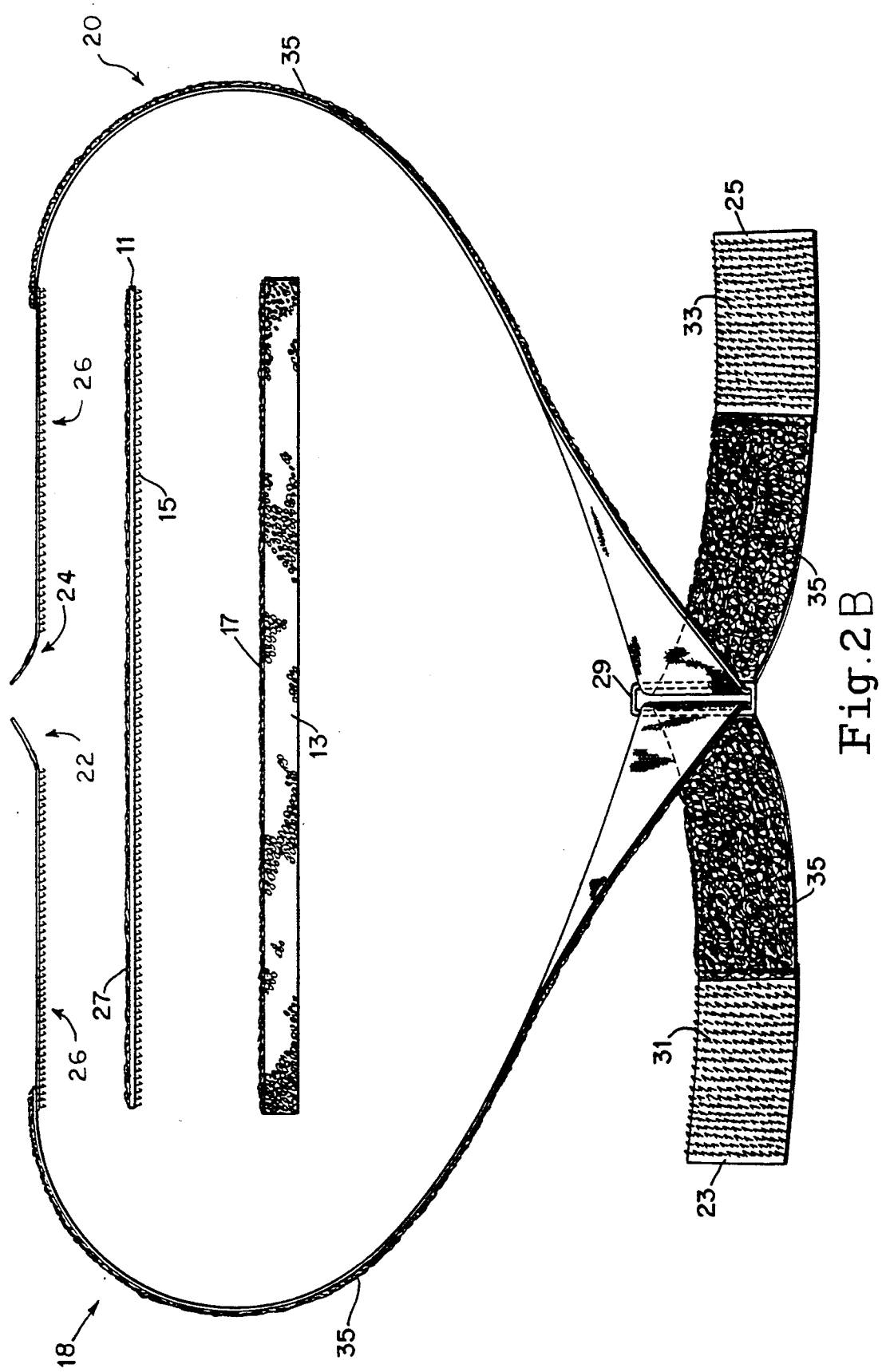
FIG. 2B is a top assembly view of a dual strap embodiment of the present invention, illustrating the separate components.

The device, as illustrated in FIGS. 2A and 2B, includes a stiff plate member 11 which serves as the primary structural member of the device to provide shape, support and rigidity while allowing flexibility in conforming to the wearer. Pad 13 is provided between the interior surface of plate 11 and the abdomen of the wearer to provide cushioning for the wearer, as illustrated in FIGS. 1 and 3. The pad 13 is secured to the plate 11 by hook and loop interactive attachment means 15 and 17, such as VELCRO or a similar contact attachment structure. In the illustrated embodiment, the hook portion 15 is attached to the plate 11 and the loop portion 17 forms a part of one surface of the pad 13, however these could be reversed.

The pad 13 is a washable, replaceable foam pad which provides a soft conformable padding between the wearer and the plate 11. Plate 11 provides the necessary shape integrity to provide proper support and maintain adequate retention without unnecessarily incumbering the wearer. Plate 11 extends above the waist of the wearer to a height along the abdomen sufficient to prevent forward bending of the abdomen to reduce slumping, as the plate 11 is sufficiently rigid to resist bending under the weight of the wearer.

The plate 11 and pad 13 are held in place about the wearer by strap and buckle system which circumscribes the lower trunk of the wearer and is also secured about the chair or seat, as illustrated in FIGS. 1 and 3. The strap system, in a first embodiment illustrated in FIG. 2A, includes a single strap 19 attachable to the front surface of the plate 11 and having its ends secured by a buckle 29. The strap system, in a second embodiment of the present invention illustrated in FIG. 2B, includes two straps 18 and 20 attachable at one end to the front surface of the plate 11 and having the other ends secured by a buckle 29.

Strap 19, as illustrated in the first exemplary embodiment herein FIG. 2A, includes a series of alternating hook and loop portions. The first center portion 21, provided on a first side of the strap 19 and located about midway between the ends 23 and 25 of the strap 19, is configured to mate with a complementary portion 27 provided on the outer surface of plate 11. Strap 19 is thus removably secured to plate 11. The remaining portions of strap 19 are brought around the wearer and the ends 23 and 25 are passed through the buckle 29. The ends 23 and 25 are looped back across opposite sides of the buckle, the strap is cinched tight and the ends are secured to the strap 19 through the interaction of complementary fastener sections 31 and 33 with the surface 35 of the intermediate portions of the strap 19 between the ends and the central portion 21. The tips of ends 23 and 25 can be left bear, as illustrated, to provide a gripable surface to aid in removal of the strap.

In use, the efficient one piece buckle 29 allows for rapid and easy application of the device to the wearer, without removal or disturbance of the wearer from the seated position. As illustrated in FIG. 1, the belt secures the wearer with the plate 11 across the lower abdomen of the wearer and the strap extending around the wearer to the back of the chair where it is buckled. Placement of the buckle behind the chair allows for easy application without disruption to the wearer.

Straps 18 and 20, as illustrated in the second exemplary embodiment herein FIG. 2B, also include a series of alternating hook and loop portions. The front ends 22 and 24 are provided with an attachment surface 26 on a first side. This attachment surface 26 is configured to mate with a complementary attachment portion or surface 27 provided on the outer surface of plate 11. Thus removably securing a first end 22 and 24 of each of the straps 18 and 20 to plate 11. The first ends 22 and 24 are also provided with a bear or bald patch, as illustrated, to provide a gripable surface to aid in removal of the strap. The remaining portions of straps 18 and 20 correspond to the portions of strap 19 described above as indicated by the corresponding numbering.

With the second embodiment of the present invention, once the device has been secured about the wearer and sized, it can be removed by detachment of the front end 22 or 24 of one or both of the straps 18 or 20, and the adjustment of the buckle need not be disturbed. The device can therefore be easily reapplied without the need to readjust the buckle as with the first embodiment.

Figure 5:
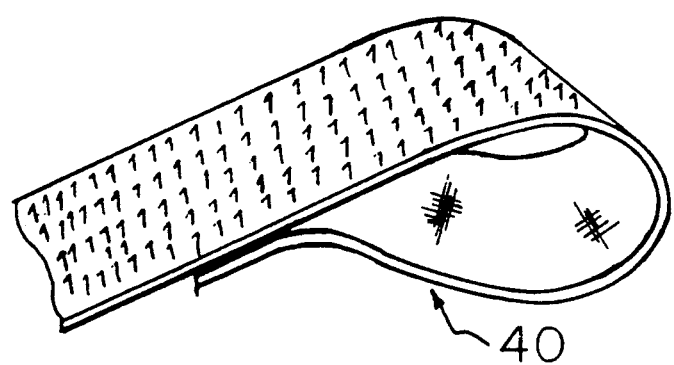
FIG. 5 is a perspective view illustrating a loop alternative for the ends of the straps of the present invention.

As illustrated in FIG. 5, the ends of the straps alternatively can be formed into a loop 40 by looping back a portion of the end of the strap and secured it to the strap. This provides a hole for gripping the end to aid in release of the strap. The wearer or attendant personnel can place a finger or other instrument in the loop to grasp the strap for removal.

Figure 4B:
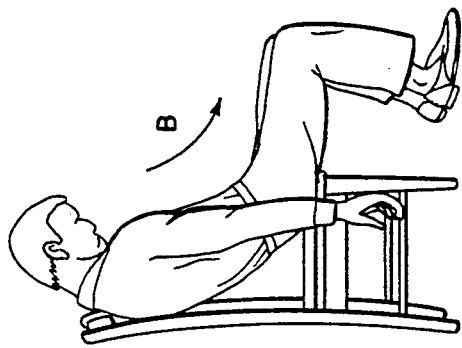
FIG. 4A is a diagrammatic view illustrating the motion of slumping and FIG. 4B illustrating the motion of slipping.
Figure 4A:

FIG. 4A illustrates slumping, arrow A, and FIG. 4B illustrates slippage, arrow B. After the strap 19 or straps 18 and 20 are positioned about both the wearer and the seat, as illustrated in FIGS. 1 and 3, the plate 11 acts to retain the wearer and to provide posture support. Plate 11 is of sufficient height and rigidity to resist bending of the wearer and thereby reduces slumping. The belt or strap is secured sufficiently tight to retain forward motion of the lower body of the wear to prevent movement between the belt and the wearer which allows for slipping.

The plate 11 is constructed of a rigid material resistant to sharp bending yet pliable enought to form a slightly curved shape in order to be conformable to the contour of the wearer's abdomen. The plate can be constructed of plastic such as rigid polyethylene or PVC, or can be of metal or composite material. It is preferable to construct the plate 11 out of material which can be easily cleansed and sterilized.

The plate 11 is of sufficient height to prevent the wearer from bending about the abdomen in the manner illustrated in FIG. 4A. In FIG. 4A, the illustrated individual is not provided with any support and therefore is able to slump freely through bending of the spine as the abdomen collapses. The belt of the present invention provides a degree of rigidity to the spine through containment of the lower abdomen and prevents slumping by spanning a sufficient height to prevent the upper abdomen from approaching the wearers thighs.

The pad 13 is constructed of a non-rigid foam material providing cushioning between the plate 11 and the wearer. The pad 13 is removable and is also preferably made of a material which can be easily cleansed and sterilized. Further, it is preferable that the pad 13 be disposable so that sterility can be easily achieved through replacement. The cushioning of the pad 13 will diminish with use, therefore necessitating replacement of the pad more often than replacement of the plate 11. The removable design of the present invention allows for ease of replacement.

The strap 18, 19 and 20 are preferably constructed of a strong non-stretch material such as nylon to allow for tight securing of the plate 11 in proper position. The straps can be constructed of a single continuous ribbon of base material with the appropriate VELCRO or equivalent material sections formed therein. Manufacture of a continuous strip eliminates seams which can fail to the detriment of the support provided by the device of the present invention. Further, the continuous strip simplifies manufacturing and eliminates potential discomfort to the wearer.

The strap can be tightened to a sufficient degree to retain the wearers back firmly against the chair back to prevent separation which can lead to slippage as illustrated in FIG. 4B. The prevention of slumping and slippage not only increases the belts effectiveness in providing proper support, but also increases the effectiveness of the posture support provided. The relief of stress and strain in the wearers back allows for prolonged seating with reduced discomfort and fatigue.

As illustrated in FIGS. 1 and 3, the strap extends behind the seat without direct connection to the seat. By not requiring connection to the seat, the device is universal and does not require a specific seat construction for implementation.

Because many varying and different embodiments may be made within the scope of the inventive concept herein taught, and because many modifications may be made in the embodiments herein detailed in accordance with the descriptive requirements of the law, it is to be understood that the details herein are to be interpreted as illustrative and not in a limiting sense.

I claim:
1. A belt for providing support to a seated wearer, comprising:
    an essentially planer semi-rigid plate;
    strap means removably attached to said plate for positioning said plate adjacent the abdominal area of the wearer;
    cushioning means removably attached to said plate between said plate and said wearer, wherein said strap means includes a single continuous strap having:
        a first center portion having first releasable contact attachment means on a first surface thereof,
        first and second end portions having second releasable contact attachment means on a first surface thereof, and
        first and second intermediate portions having third releasable contact attachment means complementary to said second attachment means on a first surface thereof.
2. The belt of claim 1, wherein said plate includes releasable contact attachment means complementary to said first attachment means of said strap.
3. The belt of claim 1, wherein said plate spans essentially the front surface of the lower abdomen of said wearer.
4. The belt of claim 1, wherein:
    said strap is elongated for extending around the trunk of said wearer and the article upon which the wearer is seated.
5. The belt of claim 1, further comprising:
    a buckle for receiving and securing said strap behind said wearer.
6. A belt for providing support to a seated wearer, comprising:
    an essentially planer semi-rigid plate;
    strap means removably attached to said plate for positioning said plate adjacent the abdominal area of the wearer;
    cushioning means removably attached to said plate between said plate and said wearer, wherein said strap means includes two straps, each having:
        a first end portion having first releasable contact attachment means on a first surface thereof,
        a second end portion having second releasable contact attachment means on a first surface thereof, and
        an intermediate portion between said first and second ends, having third releasable contact attachment means complementary to said second attachment means on a first surface thereof.
7. The belt of claim 6, wherein said plate includes releasable contact attachment means complementary to said first attachment means of said straps.
8. The belt of claim 6, wherein
    said plate spans essentially the front surface of the lower abdomen of said wearer.
9. The belt of claim 6, wherein:
    said strap is elongated for extending around the trunk of said wearer and the article upon which the wearer is seated.
10. The belt of claim 6, further comprising:
    a buckle for receiving and securing said strap behind said wearer.
11. A belt for providing support to a seated wearer, comprising:
    an essentially planer semi-rigid plate;
    strap means removably attached to a first surface of said plate and having first and second ends extending from said plate, for positioning said plate adjacent the abdominal area of the wearer;
    cushioning means removably attached to a second surface of said plate between said plate and said wearer; and
    a buckle for receiving said strap ends for securing said strap, wherein said strap includes:
        central releasable contact attachment means on a first surface of said strap,
        end releasable contact attachment means on a second surface of said strap, adjacent each of said strap ends, and
        intermediate releasable contact attachment means complementary to said end attachment means on said second surface of said strap and located between said end means and said central means.
12. The belt of claim 11, said buckle including a single loop having opposing sides for accommodating opposite ends of said strap, wherein:
    each end of said strap overlaps a respective side of said buckle loop.
13. The belt of claim 11, wherein said plate spans essentially the front surface of the lower abdomen of said wearer.

14. The belt of claim 11, wherein:

said first and second strap ends are elongated for extending around the trunk of said wearer and the article upon which the wearer is seated.

15. The belt of claim 11, wherein:

said buckle is configured for positioning behind said wearer.

* * * * *